United States Patent [19]

Maruzeni et al.

[11] Patent Number: 4,874,699

[45] Date of Patent: Oct. 17, 1989

[54] REACTION METHOD FOR TRANSESTERIFYING FATS AND OILS

[75] Inventors: Shoji Maruzeni; Wataru Matsumoto; Nozomi Yasuda, all of Tokyo, Japan

[73] Assignee: Asahi Denka Kogyo Kabushiki Kaisha, Tokyo, Japan

[21] Appl. No.: 898,513

[22] Filed: Aug. 21, 1986

Related U.S. Application Data

[63] Continuation of Ser. No. 611,964, May 18, 1984, abandoned.

[30] Foreign Application Priority Data

| May 19, 1983 | [JP] | Japan | 58-88167 |
| Jul. 12, 1983 | [JP] | Japan | 58-126392 |
| Mar. 26, 1984 | [JP] | Japan | 59-57739 |

[51] Int. Cl.$^4$ .............................................. C12P 7/62
[52] U.S. Cl. ................................................... 435/135
[58] Field of Search ........................................ 435/135

[56] References Cited

U.S. PATENT DOCUMENTS

| 4,167,447 | 9/1979 | Masri et al. | 435/178 |
| 4,275,011 | 6/1981 | Tanaka et al. | 435/134 |
| 4,275,081 | 6/1981 | Coleman et al. | 435/134 |
| 4,420,560 | 12/1983 | Matsuo et al. | 435/134 |

FOREIGN PATENT DOCUMENTS

2119397 11/1983 United Kingdom ............... 435/134

Primary Examiner—Douglas W. Robinson
Assistant Examiner—Joseph A. Lipovsky
Attorney, Agent, or Firm—Birch, Stewart, Kolasch & Birch

[57] ABSTRACT

A two-step reaction method for the transesterification of fats and oils, comprising hydrolyzing fats and oils to produce diglycerides by reacting said fats or oils with lipase; esterifying said digylcerides and to produce triglycerides by reacting said diglycerides with at least one fatty acid.

27 Claims, 3 Drawing Sheets

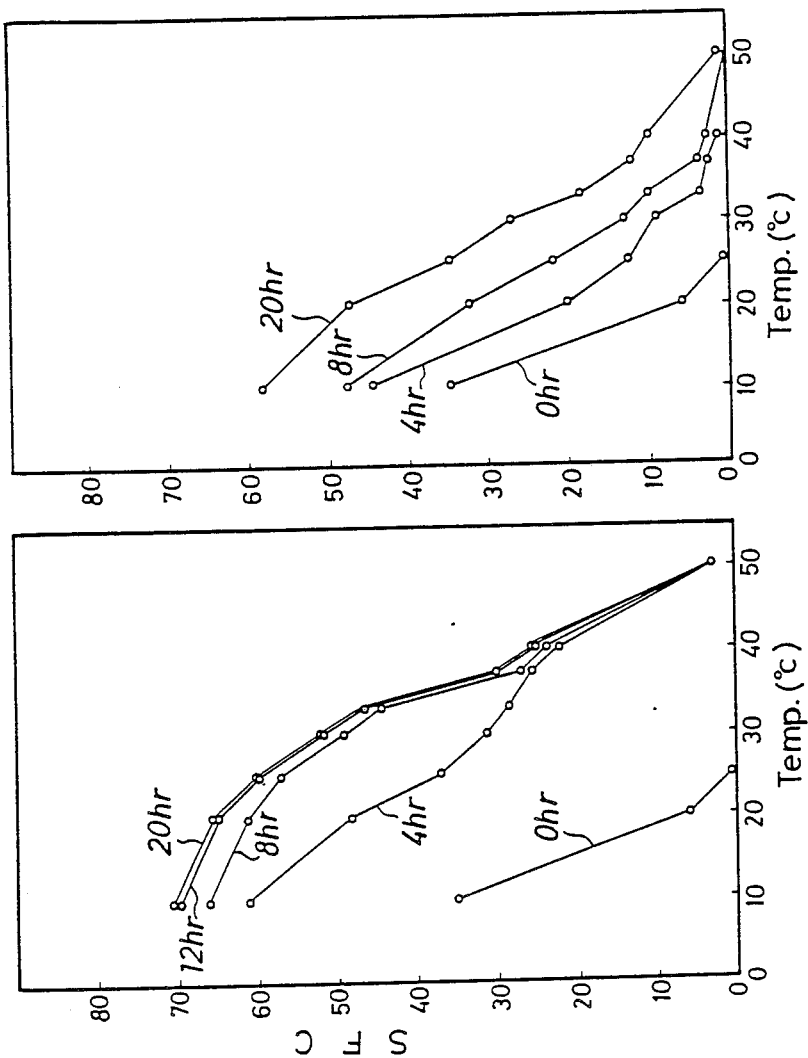

REACTION METHOD FOR TRANSESTERIFYING FATS AND OILS

This application is a continuation of copending application Ser. No. 611,964, filed on May 18, 1984, now abandoned.

BACKGROUND OF THE INVENTION

This invention relates to a method for transesterifying fats and oils using lipase, and particularly, relates to a method for performing transesterification of fats and oils by lipase with a two-step reaction comprising a hydrolysis step and an esterification step.

PRIOR ART

Transesterification reactions of fats and oils, as well as hydrogenation, are key technologies in the production of processed fats and oils. Conventional transesterification has been carried out in the presence of inorganic catalysts and the like such as metallic sodium, etc. However, this chemical process is undesirable because the fatty acid to be transesterified shows low position-selectivity for the bonding sites in glycerol.

On the other hand, it is known that lipase (E C 3.1.1.3) as an enzyme for hydrolysis catalyzes not only hydrolytic reactions, but also esterification reactions (M. Iwai, Y. Tsujisaka, J. Gen. Appl. Microbiol. 10, 13, (1964)). The transesterification of fats and oils using lipase has several advantages, such as processing at ordinary temperatures and atmospheric pressure, and so forth. Transesterification of fats and oils using lipase is expected from the point of view of energy and resources saving, due to its advantages in that the reaction is carried out at ordinary temperature and atmospheric pressure. In addition, the reaction shows high selectivity, e.g., substrate specificity, the specificity on position occuyping, etc.

In general, it is recognized as common knowledge that the enzymatic reaction shall be carried out in water solution, but in the case of the transesterification reaction of fats and oils by lipase, a reaction system with a fair amount of water causes a precedent hydrolytic reaction, and thus it is difficult to obtain a favorable reaction-product. Therefore, the previously known transesterification process of fats and oils by lipase is carried out at an extremely suppressed water level. For example, Tokkaisho No. 55-71797 (Laid-open No. 71797/80 Japanese patent application) describes a reaction system of a water concentration of less than 0.18 wt. percent for the substrate. Tokkaisho No. 52-104506 (Laid-open No. 104506/77 Japanese patent application) shows a method which is conducted under the presence of a small amount or 0.2-1 wt. percent of water for the substrate. The enzyme is, however, not fully hydrated in a reaction carried out at an extremely suppressed water content, like the above-mentioned known method, and the enzyme is not fully activated since it cannot be changed into the optimum structure for reacting, and thus, the reaction rate is very low. A complicated drying process for removing excess water from the enzymatic composition is required. Therefore, an irreversible inactivation of the enzyme is inevitable, and the adjustment of the drying time and the ratio of water content are very empirical, and thus, stable reaction processing is not achieved. Furthermore, in the case of the repeated use of the enzymatic composition, enzymatic activity gradually decays, due to the gradual decrease of water in the enzymatic composition.

Accordingly, it is necessary before processing to add a very small amount of water again, but the adjustment of the amount of water to be added to the reaction system is very difficult.

As mentioned above, the transesterification reaction of fats and oils by lipase has more advantages than the chemical method using an inorganic catalyst, but conversely, it has many difficulties and those difficulties must be solved in order to utilize them in industrial applications.

BRIEF SUMMARY OF THE INVENTION

The object of this invention is to develop a reaction method for maintaining a stabilized reaction and for increasing the reaction rate to a level capable of industrial use, by fully activating lipase in the reaction system, so as to attain an industrial use of transesterification of fats and oils by lipase.

Further, another object of this invention is to enhance the economical efficiency of the reaction process of transesterification, by preventing inactivation of lipase in the reaction system to enable lipase to be used repeatedly.

The inventors have been earnestly involved in investigations in connection with the transesterification reaction of fats and oils by lipase, with an attempt to attain the above-mentioned objects and as a result, now they are able to make available a reaction capable of displaying the full function of lipase.

Concerning lipase, its utility has been already proved by precursory investigations (See e.g. (1) J. Gen. Appl. Microbiol. 10, 13, (1964), (2) Biochem. Biophys. Acta. 489, 415, (1977), (3) ibid, 575, 156, (1979), and (4) Agric. Biol. Chem. 40, 655 (1976), etc.) by Tujisaka, Iwai et al., which disclose that lipase can be used as a catalyst for the esterification reaction which is a reaction of substrate specificity and a reverse reaction of hydrolysis. In this context, it has also been experimentally proven that position specificity at glycerol in the case of esterification conforms with hydrolysis, and that the final synthesized ratio of glyceride from glycerol and fatty acids by lipase is governed by the water content in the reaction system.

DETAILED DESCRIPTION OF THE INVENTION

The present inventors have analyzed the transesterification reaction of fats and oils based upon the above-mentioned facts from the standpoint of reaction engineering and, as a result, have discovered that the reaction rate (r) in the transesterification of fats and oils is basically represented by the following equation:

$r = K (DG) (FA)$ wherein K is the overall reaction rate constant, (DG) represents the concentration of diglyceride and (FA) represents the concentration of fatty acids. K depends significantly on the water content in the reaction system. The investigation of the reaction rate of the transesterification reaction of fats and oils has seldom been reported until now.

The present inventors have conducted a basic investigation and study on the rate of the transesterification reaction of fats and oils by a simplified system which consists of trilaurin and capric acid. An computer analysis with equations of the reaction rates based on all possible reaction pathways which correspond to the changes by time, was conducted. As a result of this analysis, it is concluded that glyceride and fatty acid change the fatty acid radicals directly, and thus, the reaction to produce new glyceride never happens.

On the other hand, the experimental data agree with the calculated data, which was obtained under the assumption that the new triglyceride should be formed by the esterification of diglyceride and fatty acid. In other words, it was assumed that diglyceride should be an intermediate in the transesterification reaction, and thus, the above-mentioned basic equation was introduced.

Furthermore, detailed studies were repeated on the transesterification reaction between fatty acids and alcohols by lipase and it was discovered that this esterification reaction progresses so rapidly so that once produced esters are seldom hydrolyzed.

The reaction method of this invention for the transesterification of fats and oils by lipase is based upon knowledge that diglyceride is an intermediate in the transesterification reaction of fats and oils, and is further based upon the conception that diglyceride, which has been usually considered as an unfavorable by-product, shall be included in the reaction and therefore the reaction equilibrium is adjusted artificially.

The method of this invention for the transesterification of fats and oils is characterized by conducting the transesterification reaction in two steps, wherein the first step is the hydrolysis of fats and oils by lipase, and the second step is the esterification of glyceride by lipase, and this reaction is a successive process. The operation of bath placements for a multi-step purpose is also able to be adopted to increase the reaction yield.

The method of this invention for the transesterification of fats and oils is favorably carried out by adding alcohol to the reaction system.

Preferred alcohols used in this invention are aliphatic alcohols having 4-18 carbon atoms, and more preferably, butanol, hexanol, octanol and dectanol. Alcohol may be added to either the first or second step, and preferably, should be added to both the first and second steps. During the first hydrolysis step, it is favorable to add alcohol at the initial time of the reaction. By adding alcohol at this time, the free fatty acid resulting from the hydrolysis is converted into alcohol ester and this alcohol ester is hydrolyzed a very low degree. Thus, the hydrolysis of glyceride is greatly accelerated. The amount of alcohol to be added at the first step is an equimolar amount or less corresponding to the free fatty acid amount to be produced by the hydrolysis, and favorably, it is a proportionated amount to 50-90 mol % of the free fatty acid estimated to be produced.

On the other hand, at the second step (which is the step of the esterification reaction by the addition of fatty acid), partial glyceride (which is mostly diglyceride) is esterified to produce triglyceride. After the proposed triglyceride composition is obtained, alcohol is added to the composition to change the majority of the free fatty acid remaining to alcohol ester. In this case, the amount of alcohol to be added at the second step may be the equimolar amount or less for the remaining free fatty acid after triglyceride has been produced, and the alcohol amount corresponding to 50-90% of the remaining free fatty acid is favorable.

This conversion of free fatty acid into alcohol ester has the advantage that the recovery of the triglyceride after the reaction is facilitated.

Lipase used in the reaction method of this invention for the transesterification of fats and oils by lipase is favorably included with a carrier therefor, such as diatomaceous earth, active carbon, gypsum, geolite, cellulose and the like, and particularly preferred is a carrier comprising porous solid and chitosan or its derivative whereby lipase is fixed on the carrier. Favorable porous solid constituting the carrier is one or more selected from the group consisting of FLORISIL (registered trademark; an activated magnesium silicate), diatomaceous earth, CELITE (registered trademark; siliceous earth), silica gel, terra alba, corncob and sawdust.

Favorable chitosan or its derivative constituting the carrier is one or more selected from the group consisting of chitosan, N-acyl chitosan, N-mixed acyl chitosan, N,O-acyl chitosan, N-allylidene chitosan, N-alkylidene chitosan, salt of chitosan and those partially reacted. "Partially reacted" means the compound produced from the reaction of the functional group of chitosan, wherein the amino group or hydroxy group is partially reacted. Further, as chitosan derivatives, the deacetylized product from the homogenous reaction system of chitin which have 40-60% of a deacetylation ratio, also may be used effectively.

The carrier of the fixed lipase used in this invention still may contain a resin having a strong water absorptiveness, and this kind of resin is a water-absorptive polyurethane resin, polyhydroxyethyl methacrylate, polyacrylic resin, starch-acrylic acid graft polymer (starch is graft-polymerized with acrylic acid, and the resultant product is neutralized, then bridged by a small amount of bridging agent to obtain the resin), starch-acrylonitrile graft polymer (obtained by the graft-polymerization of the starch with acrylonitrile by radioactive rays of second Cerium salt, then hydrolytic decomposition, then the purification and drying), process starch obtained by carboxymethylating the starch with monochloroacetic acid and bridging with formalin, cellulose-acrylonitrile graft polymer, processed cellulose obtained by carboxymethylating the cellulose with monochloroacetic acid and bridging with formalin, a self-bridged product obtained from the hydrolysis of vinyl alcohol-acrylonitrile copolymer or vinyl acetate-methylmethacrylate copolymer, polyvinyl alcohol inter-bridged obtained by the radioactive treatment of dialdehyde, bridged polyethyleneoxide, etc. These resins having strong water absorptiveness may be used alone, or a combination of two or more of them can also be used.

Among such resins having a strong water absorptiveness, starch-acrylic acid graft copolymer, and a self-bridged product obtained from the hydrolysis of copolymer of vinyl alcohol-acrylic acid or vinyl acetate-methylmethacrylate may be used favorably, and the former can be commercially available SANWET IM-300 (registered trademark, made by Sanyo Chemicals Co. Ltd., Japan). The latter can be SUMICAGEL S-50 (registered trademark, made by Sumitomo Chemical Co. Ltd., Japan). The preferred ratio of the chitosan derivative to the porous solid is 0.05-1 part by weight of the chitosan derivative per 1 part by weight of the porous solid, and an even more preferred ratio of the chitosan derivative is 0.1-0.5 part by weight per 1 part by weight of the porous solid. The use of the resin having strong water absorptiveness is preferably 0.05-1 part by weight per 1 part by weight of the porous solid, more preferably 0.1-0.5 part by weight per 1 part by weight of the porous solid.

The fixed lipase used in this invention is prepared according to a method for preparing the fixed enzyme, characterized by forming the gel of the chitosan derivative, dispersing the porous solid into the gel and drying this dispersion to obtain a carrier, then fixing the lipase onto the carrier.

An effective fixing of enzyme is attained by drying the dispersion and pulverizing it to obtain the carrier. Thereafter, it is mixed into an aqueous solution or buffered solution of enzyme.

Alternatively, effective fixation is obtained by mixing enzyme powder with the dried, pulverized carrier, and then adding water or buffered solution to the carrier, with continuous mixing.

A method for dispersing porous solid into the gel of chitosan derivative and then drying it may be conducted by the use of a process consisting of dispersing it in acetone with stirring; a process consisting of forming a thin layer and then drying it with air; a process of spray drying; or a process of freezedrying.

Alternatively, fixed lipase used in this invention also may be produced by a method in which the resin having strong water absorptiveness is added to the dried up dispersion comprising chitosan and porous solid, and the resultant is mixed on enzyme which is absorped in a similar manner to that mentioned above.

The structure of the fixed lipase produced by the abovementioned method is that the surface of porous solid is covered with the gel of chitosan derivative, and further, lipase is fixed to this chitosan gel by a mode such as absorption, inclusion, or ionic combination.

It is conceived in the case of the system containing resin having strong water absorptiveness that the surface of the porous solid is covered with a gel comprising chitosan derivative and resin having a strong water absorptiveness, and further, that lipase is fixed to that gel mixture by absorption, inclusion, or ionic combination. The above-mentioned fixed lipase used in this invention has a great surface area and high activity due to the above-hypothesized structure.

The selection of the diameter of the porous solid facilitates the separation and recovery of the fixed lipase. Both the surface and inside of the fine pores, which are made of chitosan derivative and resin having strong water absorptiveness, have the characteristic that both of these are able to change the water content of the surface and the inside, which causes the reaction of lipase.

It is possible with the above-mentioned fixed lipase that not only the necessary amount of water for activating enzyme, but also the necessary amount of water for reacting, can be retained.

In the case of the hydrolytic reaction, usually the reaction system has been a non-homogeneous system consisting of water and substrate, and in such a reaction system, the production of emulsion has been effected at interfaces, and frequently, the difficulty has been with the separation of the decomposed material from the desired product. Production costs have increased due to a reduction in operability and a lowered recovery ratio of the product.

However, in the case of the hydrolytic reaction as the first reaction step of this invention using fixed lipase, since the required amount of water for the hydrolytic reaction can be retained in the inside of the fixed lipase, the reaction of this invention can be conducted in a reaction system in which free water is not substantially contained. Thus, essentially no emulsion is generated, and easy separation of decomposed material and the heightened recovery ratio of the product are realized.

In the case of the esterification reaction or transester group reaction, non-aqueous systems have been frequently seen, and with this non-aqueous system, the apparent decrease of enzymatic activity due to the temporary ceasing of enzymatic activity, which is caused by the decreasing amount of water in the reaction, not always conforms with an essential inactivation of enzyme.

However, in the case of the esterification reaction as the second step of this invention using fixed lipase, the supply of the necessary amount of water for exhibiting enzymatic activity is easily facilitated. Therefore, stable emergence and maintenance of enzymatic activity are the result.

In the case of the hydrolytic reaction of the first step of the reaction of this invention, the use of the fixed lipase is desirably 3–40%, and more desirably, 6–20% for the substrate (fats and oils).

The use of the enzyme of 5–2000 U/g for the substrate is preferred and, more desirable is 50–500 U/g. In the case of the esterification as the second step of the reaction, the use of the fixed lipase for the substrate is preferably 0.5–10%, and more preferably, is 1.0–5.0%.

As the amount of enzyme for the substrate, 20–10000 U/g is preferred and 100–1000 U/g is more preferred. Regarding the activity unit (U) of enzyme, when the enzyme is added into 5 ml of emulsified olive oil liquid and 4 ml of 0.1M phosphate buffered solution, then reacted for 30 minutes at 37° C., each produced fatty acid corresponding to 0.06 ml of 0.05N sodium hydroxide solution is determined as an activity unit (U). Enzymatic activity shown in the examples hereinafter has the same meaning. Fats and oils as the substrate used in the method of this invention for transesterifying fats and oils by lipase, are usual vegetable and animal fats and oils or processed fats and oils, or mixtures thereof. Examples are soybean oil, cocoanut oil, sunflower oil, rapeseed oil, olive oil, corn oil, cotton seed oil, tallow, lard, fish oil, etc.

When a glyceride having a particular formulation and being raw material for the substrate of cocoa butter (e.g., 1,3-distearo-2-oleoglyceride, 1,3-palmito-2-oleoglyceride) is the object for the transesterification reaction, fats and oils containing a large quantity of oleic acid at the 2-position of glyceride may be used. Examples are olive oil, camallia oil, sasanqua oil, palm butter, sal butter, illipe oil, kokum butter, Shea butter, mowrah oil, phulwara butter, Bolneo tallow or fractions thereof.

At the first step, i.e., the reaction step dominated by the hydrolytic reaction, the method of the present invention is preferably conducted in a reaction system to which a large amount of water is added.

It is preferable that 0.01 parts by weight or more, preferably 0.02 parts by weight or more of water per 1 part by weight of fats and oils, is added and by the addition of this range of the amount of water, the reaction reaches an equilibrium together with the mixing and stirring for 1–4 hours at 20°–50° C., which temperature range causes an ordinal enzymatic reaction. Thus, the reaction product having 15–50 wt. % of diglyceride content for total glyceride, or having 15–70 wt. % of diglyceride content when alcohol is added, is obtained.

The optimum amount of water is 0.02–0.10 parts by weight per 1 part by weight of fats and oils and by these relative amounts, the reaction product containing 20–40 wt. % of diglyceride for total glyceride, 20–60 wt. % in the case of the addition of alcohol, is obtained.

Then, at the second step, i.e., the reaction step dominated by the esterification reaction, fatty acid is added to the reaction product which has been produced by the first step, and mixing and stirring is continued while maintaining the temperature at 20°–50° C.

By the addition of fatty acid, the reaction system rapidly shifts from hydrolytic reaction to an esterification reaction. Diglyceride which has been produced at the first step is esterified by the esterification reaction and triglyceride is obtained.

As the lipase used in this invention, that of the Rhizopus group, the Aspergillus group, the Candida group, the Mucor group and Pancreas lipase, etc., may be used. Almost all of these are commercially available. Among these, lipase having 1,3-position specificity for triglyceride are particularly favorable; and lipase falling in this category are of Rhizopus delemar, Rhizopus japonicus, Mucor japonicus and so forth.

In a preferred embodiment, the hydrolytic reaction is carried out in such a manner that the ratio of 1,2 (2,3) -diglyceride in the total diglyceride produced at the first hydrolytic reaction step reaches 70 wt. % or more preferably, 90 wt. % or more, and thus, a selective transesterification reaction is attained.

Since diglyceride has an unstable structure which frequently causes an acyl group-transfer reaction, it is desirable to lower the temperature under 40° C. with the hydrolytic reaction. It is also desirable to end the reaction within 10 hours in the case of a reaction temperature of 40° C.

Another preferred embodiment is characterized by the removal of water existing in the reaction system at the second step esterification reaction. At the esterification step, the reaction equilibrium shifts quickly with the addition of fatty acid, and the rate of the esterification reaction is again accelerated by the removal of water existing in the reaction system, while the rate of the hydrolytic reaction is gradually decreased.

The removal of water existing in the reaction system at the esterification step can be conducted effectively by introducing a dried inert gas into the reaction system and then exhausting it from the reaction system with the association of water. Such inert gas may be nonexplosive, and for fats and oils, the gas can be nitrogen gas, argon gas or helium gas.

The introduction of the inert gas into the reaction system may be conducted by bubbling it into the liquid phase in the reactor, in addition to blowing to the gaseous phase.

During the association and removal of water by using the inert gas, mixed exhausted gas is passed through a condenser to be cooled to a temperature less than the freezing point of water by using a cooling medium. In the condenser, water contained in the mixed gas is converted to ice to be trapped and thus, the water vapor is fully separated from inert gas.

Again, the separated gas is reused by its return to the inside of the reaction system.

The amount of fatty acid to be added at the second step (esterification reaction) of the method of this invention is, preferably 0.4–2.0 part by weight per 1 part by weight of fats and oils. Fatty acids which can be used have a carbon number of 2–22 of the straight chain saturated or unsaturated type, e.g., palmitic acid, stearic acid, oleinic acid, etc.

The above-mentioned fatty acid can be used so that all parts of the prescribed amount are added at once, otherwise, the addition is performed gradually with the progress of the reaction. For instance, among many fatty acids, the use of stearic acid or palmitic acid having a high melting point, has a tendency to produce a nonhomogeneous state. In such a case, the fatty acid may be dissolved in the inert organic solvent for lipase to make a homogeneous system, and thereafter the reaction is conducted. Solvents of this kind are n-hexane, hexane for industrial use, petroleum ether and the like, and they may be used in 1–10 parts by weight per 1 part by weight of fatty acid.

Regarding the reaction temperature in this invention, both the first reaction step (hydrolytic reaction) and second reaction step (esterification reaction) can be conducted at 20°–70° C. similar to an ordinary enzymatic reaction.

However, it is not suitable in the case of the first reaction step to have a temperature of 50° C. or more. The temperature should be below 40° C. because the acyl group-transfer reaction of the diglyceride produced depends on the reaction temperature.

As mentioned above, the method of this invention is a transesterification reaction by a two-step reaction including a hydrolytic reaction and esterification reaction. Therefore, in comparison to a reaction system which uses a small amount of water, the present invention enables an effective reaction, in contrast to a conventional one-step reaction which has to sacrifice the rate of the reaction to suppress the degree of formation of partial glyceride to be produced by hydrolytic decomposition. The method of this invention facilitates both an extreme increase in the reaction rate and a significant decrease of the content of partial glyceride (such as diglyceride and monoglyceride) in the final product. The increase of the reaction rate facilitates not only the reduction of the operation period of the reactor and the realization of an effective and highly productive process, but also the shortening of the residence time of the enzyme or enzymatic composition in the reactor. Therefore, the inactivation of enzyme or the deformation of the enzymatic composition caused by the stress effected by stirring or by physical change in the reactor, is alleviated.

The method of this invention eliminates complicated and troublesome labor and an unreasonable drying operation, both of which are common in the conventional process of preparing an enzymatic composition.

In the conventional method which uses an extremely small amount of water, it is necessary to adjust the initial amount of water strictly. In contrast, this invention is able to remove water easily by a removal operation at the second reaction step. When water exists in the range of 3–10 wt. % for the substrate fats and oils, a significant effect on the operativeness is rendered. Furthermore, with the method of this invention, it is not necessary to adjust the amount of water strictly for the repeat use of enzyme (lipase), and enzyme is activated again by adding water to the reaction system at the second reaction or any reaction thereafter to enable stable processing.

Moreover, it is possible with the method of this invention to use enzyme more than five times, and thus, the economy of the process is improved significantly.

Furthermore, it is proposed with the method of this invention that above-mentioned advantages are still promoted by the addition of alcohol together with lipase, by the use of lipase fixed on a carrier solid, and by the addition of alcohol together with the use of the lipase fixed on the carrier solid.

These and other advantages will be clear from the following detailed examples and descriptions taken in conjunction with the accompanying drawings, wherein:

FIG. 2 is a graph showing the change with time of the SFC (Solids Fat Content) of the triglyceride fraction contained in the reaction mixture at the second reaction step (esterification reaction) in Example 1;

FIG. 3 is a graph showing the change with time of the SFC of the triglyceride fraction contained in the reaction mixture at the transesterification reaction in Comparative Example 1;

Figure 4:
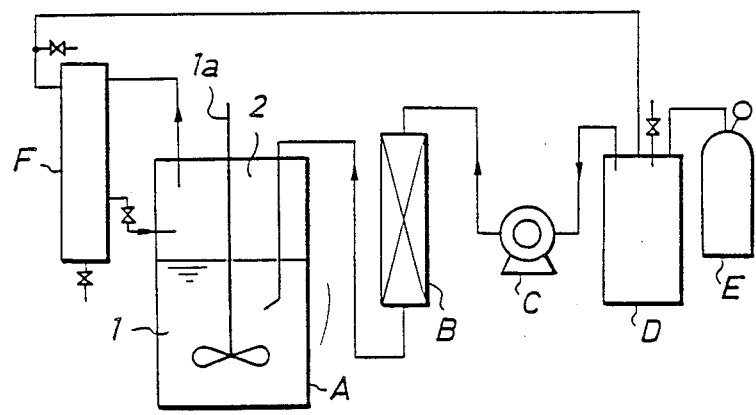
Figure 5:
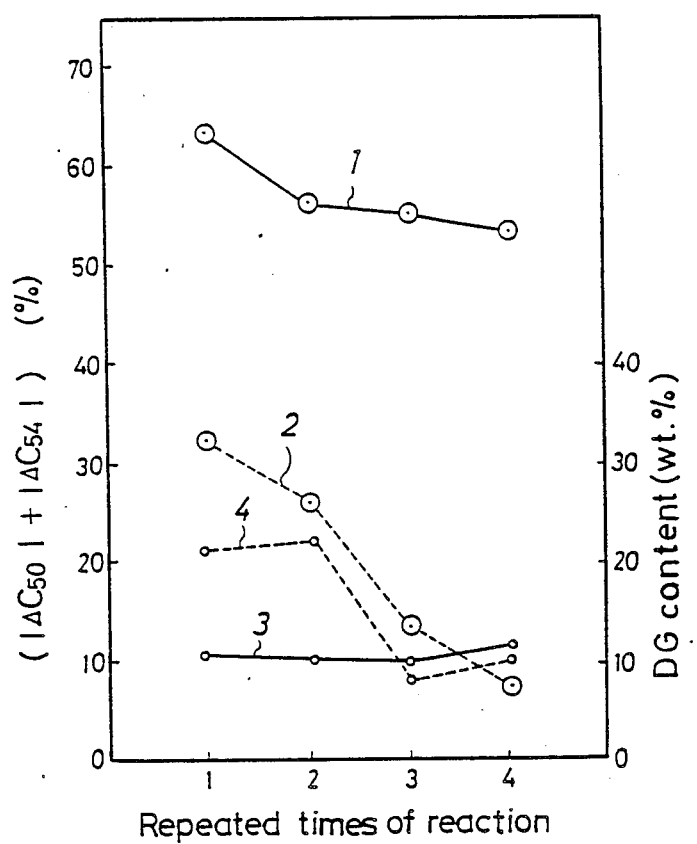

FIG. 4 is a simplified flow sheet showing an arrangement of the preferred apparatus for performing this invention and used in examples 2 and 4, wherein A is a reactor, B is a drying layer filled with drying agent, C is a pump, D is a nitrogen reservoir, E is a nitrogen bomb (cylinder), F is a condenser, 1a is a stirrer, 1 is liquid phase, and 2 is gas phase;

FIG. 5 is a graph showing the change of the triglyceride concentration and the diglyceride concentration in the reaction mixture in the case of a repeat reaction in Example 3 and Comparative Example 4.

EXPERIMENTAL EXAMPLE 1

8 g of Chitosan (Fownac N, made by Kyowa Oil and Fat Co. Ltd., Japan) are added into 60 g of 10% acetic acid solution with stirring to form a chitosan acetic acid salt gel, and to this gel, 440 g of water and 32 g of Celite (commercial name) are added to form a homogeneous mixture 2000 g of acetone is added with stirring, and any insoluble materials are recovered by centrifuging. The insoluble materials are added to 1000 g of acetone with mixing, then filtered and air-dried. An acetone removal treatment is conducted under vacuum to dry it, and the result is a carrier consisting of chitosan acetic acid salt-Celite.

103 mg of lipase (98000 U/g) originating from Rhizopus delemar are dissovled into 0.5 g of water, and this is absorbed on 2.0 g of the chitosan acetic acid salt-Celite carrier to obtain fixed lipase. The fixed enzyme is added to a mixture of 38 g of palm olein and 120 g of n-hexane. This mixture is stirred and subjected to a hydrolytic reaction in a closed reactor at 40° C.

Samples of the reaction mixture are collected at certain time intervals, and 1,3-diglyceride, 1,2 (2,3)-diglyceride, fatty acid, triglyceride, etc. are analyzed by the Synchrographic method (See, J. J. Szakasits et al., Anal. Chem., 45, 351 (1970), M. Tanaka et al., Lipid 15 (10), 872 (1980), etc.) using IATRSCAN TH-10, and a as developing solvent, benzene: chloroform: formic acid =70: 30: 2, is used. The result is shown in FIG. 1, wherein TG, 1,2 (2,3) -DG 1,3-DG, MG, FAA represent triglyceride, 1,2 (2,3) -diglyceride, 1,3-diglyceride, monoglyceride, and free fatty acid, respectively.

Lipase originating from Rhizopus delemar as used in this example has activity which attacks and cleaves the 1-position and 3-position. Accordingly, as will be clear from FIG. 1, the initial period of the reaction produces 1,2 (2,3)-diglyceride only. It is felt that a prolonged reaction period increases the ratio of 1,3-diglyceride, but this phenomenon is not due to the influence by lipase, but rather to the conversion of 1,2 (2,3)-diglyceride into 1,3-diglyceride by a non-enzymatic acyl grouptransfer reaction. A report by Okumura et al discusses such a transfer (See, S. Okumura, M. Iwai, T. Tsujisaka, Agric. Biol. Chem., 45, 185 (1981)).

Figure 1:
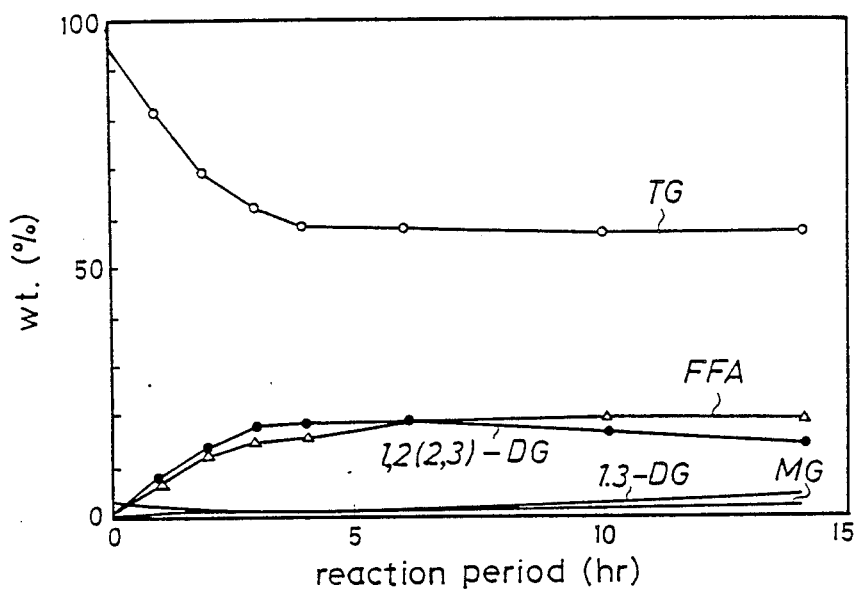
FIG. 1 is a graph showing the change with time of the concentration of each constituent contained in the reaction mixture of the hydrolytic reaction in Experimental Example 1.

If this non-enzymatic acyl group-transfer reaction is not reflected on the result, it is understood that the hydrolytic reaction reaches an equilibrium within about 3 hours, as shown in FIG. 1. The naturally prolonged reaction period causes an increased ratio of 1,3-diglyceride, and an elevated reaction temperature causes an increased rate in the enzymatic acyl group transfer reaction. When the first reaction step is dominated by a hydrolytic reaction followed by a second reaction step dominated by an esterification reaction, it is not desirable to use 1,3-diglyceride as the substrate for synthesis when using lipase having 1,3-position specificity.

Accordingly, it is desired that the hydrolytic reaction be ceased when a small ratio of 1,3-diglyceride is produced and then the reaction proceeds to the next esterification reaction step.

From this context, it is desirable to add fatty acid when the hydrolytic reaction is nearly finished.

EXPERIMENTAL EXAMPLE 2

In this example, the influence of the amount of water added to the hydrolytic reaction step is examined. Fixed enzyme is prepared by a method similar to Experimental Example 1 with the exception of a different amount of water added. Reaction conditions are similar to that of Experimental Example 1.

Using 1.3 wt. %, 2.6 wt. %, 5.3 wt. % and 10.5 wt. % of water for the substrate, each period (hours) required for attaining the equilibrium is examined and presented in Table 1.

As will be seen in Table 1, the equilibrium state of the hydrolytic reaction is determined by the initial amount of water and it is understood that increasing the amount of water causes more of an increase in diglyceride at the equilibrium state.

TABLE 1

| First step reaction (hydrolytic reaction) by each amount of water | | |
|---|---|---|
| water amount (wt. %) | period required for attaining equilibrium (hr) | DG content at equilibrium state (%) |
| 1.3 | 5.2 | 19.7 |
| 2.6 | 3.5 | 25.6 |
| 5.3 | 3.0 | 29.4 |
| 10.5 | 3.1 | 30.0 |

EXAMPLE 1

The first reaction step (hydrolytic reaction) is conducted with reaction conditions similar to that of Experimental Example 1, for 3 hours, then 57 g of stearic acid (NAA-180, made by Nippon Yushi Co. Ltd., Japan) and 165 g of n-hexane are added. The second reaction step (esterification reaction) is conducted at 40° C. Samples of the reaction mixture are collected at timed intervals, and triglyceride sections thereof are collected by using column chromatography (conduction of column chromatography; carrier, Florisil, developing agent, n-hexane: ethyl ether =85:15).

Solid fat content (SFC) is determined on triglyceride sections. As a conditioning for the determination of the SFC, these fats and oils are liquified completely and then allowed to stand for 30 minutes at 0° C. to harden the fats and oils. Thereafter, they are allowed to stand for 2 hours at 20° C. A procedure wherein they are allowed to stand for 1 hour at 30° C. and for 2 hours at 20° C. is repeated seven times. The determination of the SFC is conducted by using (PRAXIS MODEL) SFC-900, in accordance with the conventional method (A.O.C.S. Recommended Practice Cd 16-81 Solid Fat Content). SFC of triglyceride sections by 0, 4, 8, 12 and 20 hours of each reaction period at the second reaction step (esterification reaction) is shown in FIG. 2. As will be seen by FIG. 2, a negligible change on physical characteristics is noted in the case of a reaction period of 8 hours or more.

Consequently, in the case of the manufacture of the substitute for cocoa butter, it is understood as a favorable mode that the reaction is ceased after a period of about 8 hours and thus a triglyceride section having a medium melting point is fractionally collected.

COMPARATIVE EXAMPLE 1 (Includes no two-step reaction)

Transesterification is conducted under conditions similar to Experimental Example 1, with the exception that 57 g of stearic acid (NAA-180, made by Nippon Yushi Co Ltd., Japan) together with 165 g of n-hexane are added simultaneous with the addition of fixed lipase into the mixture which comprises palm olein and n-hexane, and is the same as that of Experimental Example 1.

At certain time intervals, reaction mixtures are collected fractionally, with the same mode as Example 1, and then triglyceride sections are fractionally collected through column chromatography and the SFC value is determined.

The result is shown in FIG. 3. As will be seen by FIG. 3, the change of physical characteristics by time lapse, in comparison with the result of Example 1, is very slow.

EXAMPLE 2 (Removal of water in the system at the second step), and COMPARATIVE EXAMPLE 2,3

The transesterification reaction of fats and oils is conducted by using an apparatus shown in FIG. 4. 38 g of palm olein is stirred together with the fixed enzyme and 120 g of n-hexane in the closed reactor A at 40° C. for 2 hours, to conduct the first reaction step (hydrolytic reaction). This mixed enzyme is prepared by dissolving 103 mg of lipase (98000 U/g) originating from Rhizopus delemar, into 2.0 g of water, and absorbing this on the same carrier as used in Experimental Example 1.

Stirring is stopped for a while, and during this time period, 34.2 g of stearic acid (NAA-180, made by Nippon Yushi Co. Ltd., Japan) are added, and the stirring is started again. At the same time, nitrogen gas as an inert gas from nitrogen reservoir D is, by a pump C, directed to the layer B which is filled up with a drying agent, and in which nitrogen gas is dried. This dried gas is then blown into the liquid phase 1 of the reactor A.

Inert gas is associated with the water vapor existing in phase 2, in which an equilibrium is being created between liquid and gas. Then the associated inert gas is exhausted from the reaction system, from the reactor, and thereby, the water content of the reaction system (second step reaction) is gradually lowered. At this second reaction step, the average residence time of the inert gas is approximately 3 seconds.

Then, the inert gas associated with the vapor of n-hexane and of water therein is passed into a surface condenser F which is being cooled by dry ice at about −20° C., wherein n-hexane is liquified and water vapor is changed into ice. Thus, a separated three-component phase consisting of gas, liquid and solid is formed, and the liquified n-hexane is returned to the reactor A. After the reaction is finished, stirring is ceased and the product is recovered. The product is trimethylsilylated with the use of hexamethyldisilazane (HMDS), trimethyl chlorosilane (TMCS) (made by Wako Pharmaceutical Co. Ltd., Japan) in accordance with the method of J. Blum et al (See, Lipid, 5, 601 (1970)), and is analyzed by elevated temperature gas chromatography. The result is shown in Table 2.

As shown in Table 2, by the method of this invention (Example 2), 24.6 wt. % diglyceride is produced by the hydrolytic reaction of the first reaction step, but, at the second reaction step, the amount of diglyceride is gradually decreased by the transesterification reaction and esterification reaction, and is decreased to 11.5 wt. % after 8 hours and to 7.4 wt. % after 12 hours.

As a comparative example using a fixed enzyme similar to that of Example 2, the effect of the addition of stearic acid initially (Comparative Example 2), and the effect of the coincidence of the addition of stearic acid and the use of a small amount (0.3 wt. % for substrate) of water (Comparative Example 3), are examined, and the result is shown in Table 2. Although the transesterification reaction progresses, its rate is slow in Comparative Example 2, which is a one-step reaction.

The concentration of diglyceride tends to increase before equilibrium is attained, and the decrease of diglyceride by reesterification is not noticed.

In Comparative Example 3, wherein an extremely small amount of water is added into the reaction system for the purpose of suppressing the production of diglyceride, the reaction rate is very slow. As is clear from Table 2, the reaction rate is less than 1/7 of the reaction rate of this invention. Thus, the method of Comparative Example 3 is not utilized as a practical commerical process.

The prolonged reaction time causes a significant decrease of enzymatic activity. Therefore, it is almost impossible for the reaction to reuse the recovered enzymatic agent from the finished reaction system.

TABLE 2

Transesterification reaction of palm olein - stearic acid system

| | | Fats and oils as raw material | Example 2 | Comparative example 2 | Comparative example 3 |
|---|---|---|---|---|---|
| Water amount for fats and oils (%) | | — | 5.3 | 5.3 | 0.3 |
| Hydrolytic reaction step (%) | TG | (95.3) | 73.2 | — | — |
| | DG | (4.7) | 24.6 | — | — |
| | MG | (trace) | 2.2 | — | — |
| Ester synthetic reaction step (8 hrs. of reaction period) (%) | TG C48 | (2.5) | 1.7 | 2.5 | 2.4 |
| | C50 | (42.5) | 13.6 | 28.0 | 36.8 |
| | C52 | (45.0) | 40.0 | 45.0 | 44.5 |
| | C54 | (10.0) | 44.0 | 24.5 | 16.3 |
| | DG* | (6.0) | 11.5 | 21.2 | 11.8 |

Notes) 1. TG, DG, and MG represent triglyceride, diglyceride, and monoglyceride, respectively.
2. C 48, C 50, C 52 and C 54 represent triglyceride of carbon number 48, 50, 52 and 54, respectively.
3. Numerals in column DG* represent diglyceride content (%) in total glycerides.

EXAMPLE 3 and COMPARATIVE EXAMPLE 4
(repeated reaction)

The transesterification reaction consisting of a first reaction step (hydrolytic reaction) and a second reaction step (esterification reaction) is conducted by a method similar to that of Example 2. The used fixed enzyme is recovered after the reaction is completed. Water corresponding to 5.0% for fats and oils as raw materials is absorbed on the recovered fixed enzyme.

The transesterification reaction consisting of a hydrolytic reaction step and esterification reaction step is repeated by using that fixed enzyme by a manner similar to that of Example 2. After 8 hours of the esterification reaction step, the reaction mixture is trimethylsilylated in a manner similar to that of Example 2. Then it is analyzed by elevated temperature gas chromatography, as with Comparative Example 4, and the result by reaction with the initial addition of stearic acid and with the eliminated hydrolytic reaction are analyzed in a similar manner.

From the analysis, the sum of the absolute values of the quantity of changed triglyceride having carbon number 50 (C 50) and of the quantity of changed triglyceride having carbon number 54 (C 54), which are contained in triglyceride in raw material fats and oils and in the reaction mixture, $$(|\Delta C50| + |\Delta C54|),$$

is calculated. FIG. 5 shows the result in which the result of Example 3 is presented by line 1, and the result of Comparative Example 4 is presented by line 2. Also, regarding the diglyceride content in the total glycerides in the reaction mixture, the result of Example 3 is presented by line 3, and the result of Comparative Example 4 is presented by line 4 in FIG. 5.

As will be seen by FIG. 5, the reaction rate in Example 3 is very high, and on the other hand, the reaction rate in Comparative Example 4 is significantly decreased by the influence of the repeat reaction.

EXAMPLE 4

The transesterification reaction of fats and oils is conducted by using an apparatus shown in the flow sheet of FIG. 4 as follows.

38 g of palm olein, together with 103 mg of fixed lipase on a carrier (which is prepared from lipase (98000 U/g) originating from Rhizopus delemar) is dissolved into 0.2 g of water). Then it is absorbed on the carrier similar to that of Experimental Example 1.120 g of n-hexane and 2.5 g of butyl alcohol are stirred by stirrer 1a in the closed reactor A at 40° C. for 2 hours, to conduct the first reaction step (hydrolytic reaction). After the reaction is completed, small amounts of the reaction mixture are fractionally collected, and are analyzed as described hereinafter. The result is shown in Table 3. Then stirring is stopped while 20 g of stearic acid (NAA-180, made by Nippon Yushi Co. Ltd., Japan) are added and stirring is again conducted. Nitrogen gas as an inert gas from nitrogen reservoir D is introduced by a pump C, and sent to the layer B which is filled up with a drying agent and in which nitrogen gas is dried This dried gas is then blown into the inside of liquid phase 1 of the reactor A. By exhausting the inert gas associated with the water vapor of the phase 2, in which an equilibrium is being established between liquid and gas from the reaction system, the water content in the reaction system is gradually lowered (second reaction step esterification reaction). At this second reaction step, the average residence time of the inert gas is 3 seconds. The inert gas containing vapors of n-hexane and water passes into a surface condenser F which is being cooled by dry ice at about −20° C., wherein n-hexane is liquified. Simultaneously, water is converted to ice, and a separated 3-phase mixture of gas-liquidsolid is formed, and the liquified n-hexane is returned to the reactor A. This second reaction step lasts for 12 hours.

After each reaction step is finished, a small amount of product is fractionally collected and is trimethylsilylated with hexamethyldisilazane (HMDS), trimethylchlorosilane (TMCS) (made by Wako Pharamceutical Co. Ltd., Japan) in accordance with the method of J. Blum et al (See Lipid, 5, 601 (1970)), and then analyzed by elevated temperature gas chromatography. The result is shown in Table 3.

As shown in Table 3, at the first reaction step, the amount of diglyceride contained in total glycerides is 43.3 wt. %, and monoglyceride contained in total glycerides is 7.6 wt. %.

On the other hand, about 70% of the free fatty acid produced by the hydrolytic reaction step becomes alcohol ester After the fatty acid is added, the concentrations of diglyceride and monoglyceride are gradually decreased during the second reaction step, and at the end point of the second reaction step, after a time of 12 hours, are decreased to 11.3 wt. %. The 2.0 g of n-butyl alcohol are added for the purpose of the esterification of any free fatty acid remaining in the system, and the esterification reaction of the free fatty acid is conducted at 40° C. for 5 hours. By this treatment, the acid value of the final product becomes 20.6. To recover triglyceride from the final product, a deacidifying process and distillation process are conducted easily and with a high recovery ratio

EXAMPLE 5

The reaction is conducted by a method similar to that of Example 4 with the exception of the use of n-decyl alcohol as the alcohol.

The amount of alcohol to be added is 5.3 g at the first reaction step, and the hydrolytic reaction is conducted at 40° C. for 4 hours. At the second reaction step, 20 g of stearic acid are added into the system and removal of water in the system is started and the esterification reaction is conducted with 8 hours of stirring. 5.0 g of n-decyl alcohol are added when the content of diglyceride in total glycerides is decreased to about 10%, to esterify the free fatty acid. The analysis done in a manner similar to that of Example 4 is shown in Table 4.

TABLE 3

| | Transesterification reaction of palm olein--stearic acid system (Example 4) | | | |
|---|---|---|---|---|
| | raw material % | after completion of first reaction step % | after completion of second reaction step % | final product % |
| TG | 93.1 | 29.7 (49.1) | 49.5 (88.7) | 46.9 (90.4) |
| DG | 6.1 | 26.2 (43.3) | 6.3 (11.3) | 5.0 (9.6) |
| MG | trace | 4.6 (7.6) | trace (trace) | 0.0 (0.0) |

TABLE 3-continued

Transesterification reaction of palm olein--stearic acid system (Example 4)

|  | raw material % | after completion of first reaction step % | after completion of second reaction step % | final product % |
|---|---|---|---|---|
| FFA | — | 11.1 | 23.5 | 11.5 |
| Ester | — | 28.4 | 20.4 | 36.5 |
| TG formula | | | | |
| C48 | 4.5 | 5.1 | 4.1 | 2.8 |
| C50 | 41.0 | 38.7 | 17.6 | 16.6 |
| C52 | 43.0 | 44.0 | 42.4 | 43.4 |
| C54 | 11.5 | 12.0 | 35.8 | 37.2 |
| acid value | 0.6 | 21.0 | 48.5 | 20.6 |

TG: Triglyceride
MG: Monoglyceride
DG: Diglyceride
FFA: Free fatty acids
Ester: Alcohol ester of fatty acid
Number of TG formula: Carbon number of triglyceride
Number in parenthesis shows the ratio for total glyceride

TABLE 4

Transesterification reaction of palm olein--stearic acid system (Example 5)

|  | raw material % | after completion of first reaction step % | after completion of second reaction step % | final product % |
|---|---|---|---|---|
| TG | 93.0 | 25.8 | 46.3 | 46.0 |
|  | | (52.5) | (88.5) | (90.0) |
| DG | 7.0 | 22.5 | 5.7 | 5.1 |
|  | | (45.8) | (10.9) | (10.0) |
| MG | — | 0.8 | 0.3 | 0.0 |
|  | | (1.6) | (0.6) | (0.0) |
| FFA | — | 14.1 | 21.2 | 9.78 |
| Ester | — | 36.8 | 26.5 | 39.1 |
| TG formula | | | | |
| C48 | 4.3 | 5.1 | 4.2 | 2.6 |
| C50 | 41.5 | 37.8 | 17.6 | 17.4 |
| C52 | 43.1 | 44.1 | 42.4 | 42.5 |
| C54 | 11.1 | 12.9 | 35.8 | 37.5 |
| acid value | 0.6 | 29.5 | 46.8 | 18.9 |

TG: Triglyceride
MG: Monoglyceride
DG: Diglyceride
FFA: Free fatty acids
Ester: Alcohol ester of fatty acid
Number of TG formula: Carbon number of triglyceride
Number in parenthesis shows the ratio for total glyceride

EXAMPLE 6

4.5 g of n-butyl alcohol are added into the reaction product which is prepared by the reaction according to a method similar to that of Example 4. The reaction comprises a first reaction step and a second reaction step, with the exception of no addition of alcohol at the first reaction step. Stirring is continued for 4 hours while removing water by the apparatus shown in FIG. 4, to conduct the esterification of the free fatty acid.

The result of the analysis of the esterified product is shown in Table 5.

TABLE 5

Transesterification reaction of palm olein--stearic acid system (Example 6)

|  | final product |
|---|---|
| TG | 52.1% (93.0%) |
| DG | 3.9 (7.0) |
| MG | — |
| FFA | 11.1 |
| Ester | 32.9 |
| TG formula | |
| C48 | 3.9 |
| C50 | 17.5 |
| C52 | 42.8 |
| C54 | 35.8 |
| acid value | 19.8 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A two-step reaction method for the transesterification of fats and oils, comprising:
   (a) hydrolyzing fats and oils to produce diglycerides by reacting said fats and oils with lipase having 1,3 position specificity in the presence of 0.01 to 0.10 parts by weight of water per 1 part by weight of fats and oils;
   (b) esterifying said diglycerides to produce triglycerides by reacting said diglycerides with at least one fatty acid while at the same time removing water from said reaction to increase the rate of esterification and reduce the rate of hydrolyzation, the first and/or second reaction steps being carried out by adding an aliphatic monohydric alcohol having 4 to 18 carbon atoms to the reaction system, wherein the amount of alcohol being added corresponds to 50-90 mol % of free fatty acid estimated to be produced if added in the first step, and the amount of alcohol being added corresponds to 50-90 mol. % of remaining free fatty acid, if added in the second step.

2. The method as recited in claim 1, wherein said hydrolysis of fats and oils and said esterification of said diglycerides is conducted at a temperature of 20° to 70° C.

3. The method as recited in claim 1, wherein the lipase is fixed on a carrier formed from a dispersion of a porous solid and a chitosan derivative.

4. The method as recited in claim 1, wherein said hydrolysis of fats and oils produces 15-70 wt. % of diglyceride for total glyceride.

5. The method as recited in claim 1, wherein said hydrolysis of fats and oils produces 20-60 wt. % of diglyceride for total glyceride.

6. The method as recited in claim 1, wherein said hydrolysis of fats and oils produces a diglyceride containing at least 70 wt. % of 1,2 (2,3)-diglyceride for the total diglyceride produced.

7. The method as recited in claim 1, wherein said hydrolisis of fats and oils produces a diglyceride containing at least 90 wt. % of 1,2 (2,3)-diglyceride for the total diglyceride produced.

8. The method as recited by claim 1, wherein the fatty acid is present in an amount of 0.4–2.0 parts by weight for 1 part by weight of fats and oils.

9. The method as recited by claim 1, wherein the water is removed by introducing dry inert gas during said esterification step to thereby associate the water with the inert gas and exhausting the associated water and gas from the reaction.

10. The method as recited in claim 9, wherein the associated water and gas exhausted from the reaction is passed through a condenser in which water is separated, and the inert gas is returned to the reaction.

11. The method as recited in claim 1 wherein the aliphatic monohydric alcohol to be added at the first and/or second step is selected from the group consisting of butanol, hexanol, octanol and decanol.

12. The method as recited in claim 1 wherein the amount of enzyme for the substrate at the first step is 5–2000 u/g and the amount of enzyme for the substrate at the second step is 20–10,000 u/g.

13. A two-step reaction method for the transesterification of fats and oils, comprising:
(a) hydrolyzing fats and oils to produce diglycerides by reacting said fats or oils with lipase in the presence of 0.02 to 0.10 parts by weight of water per 1 part by weight of fats and oils;
(b) esterifying said diglycerides to produce triglycerides by reacting said diglycerides with at least one fatty acid while introducing inert gas into said esterification step for removing water to increase the rate of the esterification reaction and reduce the rate of the hydrolyzation reaction, the first and/or second reaction steps being carried out by adding an aliphatic monohydric alcohol having 4 to 18 carbon atoms to the reaction system, wherein the amount of alcohol being added corresponds to 50–90 mol % of free fatty acid estimated to be produced if added in the first step, and the amount of alcohol being added corresponds to 50–90 mol. % of remaining free fatty acid, if added in the second step.

14. The method as recited in claim 13, wherein said hydrolysis of fats and oils and said esterification of said diglycerides is conducted at a temperature of 20° to 70° C.

15. The method as recited in claim 13, wherein the lipase is fixed on a carrier formed from a dispersion of a porous solid and a chitosan derivative.

16. The method as recited in claim 13, wherein the lipase has 1,3 position specificity.

17. The method as recite in claim 13, wherein said hydrolysis of fats and oils produces 15–70 wt. % of diglyceride for total glyceride.

18. The method as recited in claim 17, wherein said hydrolysis of fats and oils produces 20–60 wt. % of diglyceride for total glyceride.

19. The method as recited in claim 13, wherein said hydrolysis of fats and oils produces a diglyceride containing at least 70 wt. % of 1,2 (2,3)-diglyceride for the total diglyceride produced.

20. The method as recited in claim 19, wherein said hydrolysis of fats and oils produces a diglyceride containing at least 90 wt. % of 1,2 (2,3)-diglyceride for the total diglyceride produced.

21. The method as recited by claim 13, wherein the fatty acid is present in an amount of 0.4–2.0 parts by weight for 1 part by weight of fats and oils.

22. The method as recited in claim 13, wherein the associated water and inert gas exhausted from the system is passed through a condenser in which water is separated, and the inert gas is returned to the reaction.

23. The method as recited in claim 13 wherein the aliphatic monohydric alcohol to be added in step (a) and/or step (b) is selected from the group consisting of butanol, hexanol, octanol and decanol.

24. The method as recited in claim 13 wherein the amount of enzyme for the substrate at the first step is 5–2000 u/g and the amount of enzyme for the substrate at the second step is 20–10,000 u/g.

25. A two-step reaction method for the transesterification of fats and oils, comprising:
(a) hydrolyzing fats and oils to produce diglycerides by reacting said fats and oils with lipase at a temperature 20°–40° C. in the presence of 0.02 to 0.10 parts by weight of water per 1 part by weight of fats and oils;
(b) esterifying said diglycerides to produce triglycerides by reacting said diglycerides with at least one fatty acid, at a temperature of 20°–70° C., while introducing inert gas into said esterification step for removing water to increase the rate of esterification and reduce the rate of hydrolyzation, the first and/or second reaction steps being carried out by adding an aliphatic monohydric alcohol having 4 to 18 carbon atoms to the reaction system, wherein the amount of alcohol being added corresponds to 50–90 mol % of free fatty acid estimated to be produced if added in the first step, and the amount of alcohol being added corresponds to 50–90 mol. % of remaining free fatty acid, if added in the second step.

26. The method as recited in claim 25 wherein the aliphatic monohydric alcohol to be added in step (a) and/or step (b) is selected from the group consisting of butanol, hexanol, octanol and decanol.

27. The method as recited in claim 25 wherein the amount of enzyme for the substrate at the first step is 5–2000 u/g and the amount of enzyme for the substrate at the second step is 20–10,000 u/g.

* * * * *